US012612321B2

(12) United States Patent (10) Patent No.: US 12,612,321 B2
Hua et al. (45) Date of Patent: Apr. 28, 2026

(54) ANAEROBIC DIGESTION DEVICE FOR ORGANIC SOLID WASTE BASED ON UNCOUPLING OF HYDRAULIC RETENTION TIME (HRT) FROM SLUDGE RETENTION TIME (SRT)

(71) Applicant: Tongji University, Shanghai (CN)

(72) Inventors: Yu Hua, Shanghai (CN); Xiaohu Dai, Shanghai (CN)

(73) Assignee: Tongji University, Shanghai (CN)

( * ) Notice: Subject to any disclaimer, the term of this patent is extended or adjusted under 35 U.S.C. 154(b) by 432 days.

(21) Appl. No.: 18/449,640

(22) Filed: Aug. 14, 2023

(65) Prior Publication Data

US 2024/0025782 A1 Jan. 25, 2024

(30) Foreign Application Priority Data

Aug. 17, 2022 (CN) .......................... 202210988650.6

(51) Int. Cl.
*C02F 3/28* (2023.01)
*B01D 21/26* (2006.01)
(Continued)

(52) U.S. Cl.
CPC ............ *C02F 3/2866* (2013.01); *B01D 33/06* (2013.01); *B01D 36/001* (2013.01);
(Continued)

(58) Field of Classification Search
CPC .......... C02F 3/2866; C02F 1/004; C02F 1/24; C02F 1/38; C02F 11/04; C02F 2201/005;

C02F 2209/44; C02F 2301/046; B01D 33/06; B01D 36/001; B01D 36/045; B01D 21/267; C12M 21/04; C12M 29/18; C12M 29/20; C12M 45/04; C12M 45/06; Y02E 50/30
(Continued)

(56) References Cited

FOREIGN PATENT DOCUMENTS

| CN | 110468033 A | 11/2019 |
| CN | 111733059 A | 10/2020 |

(Continued)

OTHER PUBLICATIONS

Machine-generated English translation of CN 213895575, generated on Nov. 13, 2025.*

(Continued)

*Primary Examiner* — Fred Prince

(57) ABSTRACT

An organic solid waste anaerobic digestion device based on uncoupling of hydraulic retention time (HRT) from sludge retention time (SRT) includes a self-sustaining air flotation screening tank. A sludge pipe of the self-sustaining air flotation screening tank is connected with a first separating mechanism. A bottom of the first separating mechanism is connected with a second separating mechanism, and two separating mechanisms are connected with a return pipe of the self-sustaining air flotation screening tank. Through the two separating mechanisms, the heavy inert materials at the bottom of the self-sustaining air flotation screening tank can be subjected to swirl separation, so that the liquid part, the solid part and the gas part can be completely separated, and then the useful active materials are conveyed to the reaction device.

8 Claims, 4 Drawing Sheets

(51) Int. Cl.

| | |
|---|---|
| *B01D 33/06* | (2006.01) |
| *B01D 36/00* | (2006.01) |
| *B01D 36/04* | (2006.01) |
| *C02F 1/00* | (2023.01) |
| *C02F 1/24* | (2023.01) |
| *C02F 1/38* | (2023.01) |
| *C02F 11/04* | (2006.01) |
| *C12M 1/00* | (2006.01) |
| *C12M 1/107* | (2006.01) |

(52) U.S. Cl.
CPC ............ *B01D 36/045* (2013.01); *C02F 1/004* (2013.01); *C02F 1/24* (2013.01); *C02F 1/38* (2013.01); *C02F 11/04* (2013.01); *C12M 21/04* (2013.01); *C12M 29/18* (2013.01); *C12M 29/20* (2013.01); *C12M 45/04* (2013.01); *C12M 45/06* (2013.01); *B01D 21/267* (2013.01); *C02F 2201/005* (2013.01); *C02F 2209/44* (2013.01); *C02F 2301/046* (2013.01); *Y02E 50/30* (2013.01)

(58) Field of Classification Search
USPC ...................................... 210/195.1, 252, 259
See application file for complete search history.

(56) References Cited

FOREIGN PATENT DOCUMENTS

| | | | | | |
|---|---|---|---|---|---|
| CN | 111748451 | A | | 10/2020 | |
| CN | 112899017 | A | | 6/2021 | |
| CN | 213895575 | U | * | 8/2021 | |
| CN | 114017381 | A | | 2/2022 | |
| JP | 2002058910 | A | | 2/2002 | |
| JP | 6639330 | B2 | * | 2/2020 | |
| KR | 100816106 | B1 | * | 3/2008 | ............... B09B 3/00 |

OTHER PUBLICATIONS

Machine-generated English translation of CN 111733059, generated on Nov. 13, 2025.*

Machine-generated English translation of JP 6639330, generated on Nov. 13, 2025.*

Machine-generated English translation of KR 100816106, generated on Nov. 13, 2025.*

Machine-generated English translation of CN 114017381, generated on Nov. 13, 2025.*

* cited by examiner

ANAEROBIC DIGESTION DEVICE FOR ORGANIC SOLID WASTE BASED ON UNCOUPLING OF HYDRAULIC RETENTION TIME (HRT) FROM SLUDGE RETENTION TIME (SRT)

CROSS-REFERENCE TO RELATED APPLICATIONS

This application claims the benefit of priority from Chinese Patent Application No. 202210988650.6, filed on Aug. 17, 2022. The content of the aforementioned application, including any intervening amendments thereto, is incorporated herein by reference in its entirety.

TECHNICAL FIELD

This application relates to anaerobic digestion of waste anaerobic digestion, and more particularly to an anaerobic digestion device for organic solid waste based on uncoupling of hydraulic retention time (HRT) from sludge retention time (SRT).

BACKGROUND

The organic solid waste (kitchen waste, food waste, sewage sludge, etc.) is a multi-phase (solid-liquid-gas), multi-component (proteinoids, saccharoids, lipoids, inorganic substances, etc.) complex system with high water content (>80%). With the advancement of the national strategy of waste classification, the production of perishable organic solid waste is increasing year by year, and will seriously threaten human life and health if it is not properly handled. At the same time, it is also accompanied by the production of a large amount of $CO_2$, which will increase the carbon emissions and aggravate the greenhouse effect, thereby seriously harming the ecological environment. Anaerobic digestion stands out from a wide variety of treatment techniques due to high energy recovery and low environmental pollution, and has been widely used for waste reduction and recycling. The development of anaerobic reactor has greatly promoted the development of anaerobic digestion-based biogas production. As a micro-ecosystem for microbial growth and proliferation, the reactor is conducive to microbial stable growth and matter and energy flow, which are necessary for maintaining the continuous stability of an anaerobic treatment system.

Anaerobic digestion is a complex chain reaction process, consisting of hydrolysis, acidification, acetogenesis/dehydrogenation, and methanogenesis. Such degradation steps are performed by different communities, which have a certain relationship, and have different environmental requirements. Anaerobic bioreactors have been widely used in the field of sewage treatment, and have exhibited a remarkable treatment effect. Several types of anaerobic bioreactors have been developed, such as continuous stirred-tank reactor (CSTR), upflow anaerobic sludge blanket (UASB), expanded granular sludge bed (EGSB), and internal-loop reactor. The processing load is continuously enhanced through three iterative upgrades. However, the development of anaerobic technology in the field of organic solid waste treatment is still slow. At present, the widely-used organic solid waste anaerobic reactors are garage-type reactors and completely mixed reactors. With the progress of construction technology, there are various tank configurations (such as floating cover type, traditional type, egg type and European flat bottom type), designs (such as vertical design and horizontal design) and stirring methods (such as spiral stirring and biogas stirring). However, the maximum organic load in reactors can only reach 10 kg/m³·d, which is far from the efficiency of natural reactors evolved by "natural selection", for example, the maximum organic load of a rumen system of ruminants can reach 100 kg/m³·d (dry basis). Considering that the organic solid waste anaerobic digestion involves multiple mediums, multiple components, and complex structure, in order to improve the efficiency of anaerobic digestion for waste with high solid content, a novel organic solid waste anaerobic digestion technique and device have been developed, which is based on the spontaneous gas production ($CH_4$, $CO_2$ and so on) in the anaerobic digestion process to achieve self-sustaining air flotation of the anaerobic system (ZL201910789403.1, ZL202010672342.3 and ZL202010672330.0). The self-sustaining air flotation screening device can be arranged outside or inside the CSTR structure, and is divided into upflow zone, settling zone and recirculation zone. After the completely-mixed materials are discharged from the CSTR into the self-sustaining air flotation device, in order to enhance the mass transfer, the materials are first pushed upward in the upflow zone to overflow through the partition to fall into the settling zone, and the self-staining air flotation is achieved in this zone with a relatively stable flow. Heavy materials are discharged from the bottom, and light materials flow back into the main tank of the CSTR through the top of the screening device.

According to specific gravity, macromolecular substances in the anaerobic system (represented by humic substances) are categorized as relatively heavy components, and small molecule substances represented by microorganisms and soluble organic matters are categorized as relatively light components. These relatively heavy components are difficult to be utilized by bioconversion (i.e., inert components), and should be discharged from the system as much as possible, so as to reduce their inhibitory effect on the biological process. In contrast, these relatively light components are microorganisms which contribute to the production of anaerobic biogas or substances that are easily biodegradable (belonging to active components), and should be discharged as little as possible, so as to maintain their effective retention in the anaerobic system. Therefore, a self-sustaining air flotation screening unit is coupled with the CSTR to initially achieve the screening of refractory heavy components and active light components based on spontaneous gas production. Compared to the mixed discharging of the CSTR, only refractory heavy materials are discharged in such manner, and the active light materials flow back to the main tank of CSTR, which achieves the initial uncoupling of SRT (sludge retention time) from HRT (hydraulic retention time). This process is purely spontaneous, and achieves the separation of light and heavy components only by spontaneous sedimentation without external enhancement. There are still some active light materials remaining in the inert heavy materials at the bottom of the device, such as microorganisms or other organic materials because of the incomplete spontaneous separation. Therefore, it is urgently needed to develop an improved organic solid waste anaerobic digestion device that can enable the complete separation of heavy inert materials and light active materials to achieve the more complete uncoupling of SRT from HRT.

SUMMARY

An object of this application is to provide an organic solid waste anaerobic digestion device based on uncoupling of hydraulic retention time (HRT) from sludge retention SRT separation to solve the problems existing in the prior art.

Technical solutions of this application are described as follows.

This application provides an anaerobic digestion device for organic solid waste based on uncoupling of HRT from SRT, comprising:

a self-sustaining air flotation screening tank;

wherein the self-sustaining air flotation screening tank is provided with a sludge discharge pipe; the sludge discharge pipe is communicated with a first separating mechanism; a bottom of the first separating mechanism is connected with a second separating mechanism, and the first separating mechanism and the second separating mechanism are connected with a return pipe of the self-sustaining air flotation screening tank;

the first separating mechanism includes a shell, a first separating part and a second separating part; the first separating part and the second separating part are located in the shell, and are rotationally connected with the shell; the first separating part is located above the second separating part; and the first separating part is communicated with the second separating part; and the second separating mechanism includes a separating cylinder; a bottom of the separating cylinder is connected with a liquid collecting tank; a side of a top of the separating cylinder is provided with a first discharge port and a second discharge port.

In an embodiment, the separating section includes a rotating cylinder; an outer wall of the rotating cylinder is circumferentially fixedly connected with a plurality of upward stirring rods; a body of the rotating cylinder is provided with a plurality of through holes; the plurality of through holes and the plurality of stirring rods are in staggered arrangement; a top of the rotating cylinder is closed, and a wall at a bottom of the rotating cylinder is fixedly connected with a sprocket; the sprocket is in transmission connection with a first motor through a chain; and the first motor is fixedly connected on an outer side of the shell.

In an embodiment, the second separating part includes a cone cylinder; a top of the cone cylinder is open, and a wall of the cone cylinder is provided with a plurality of round holes; the top of the cone cylinder is fixedly connected with a cross-bar, and the cross-bar is fixedly connected with the bottom of the rotating cylinder; a bottom of the cone cylinder is rotatably connected with a cleaning pipe; an end of the cleaning pipe away from the cone cylinder penetrates a bottom of the shell and is communicated with outside; and the cleaning pipe is provided with a first valve.

In an embodiment, a part of an inner wall of the shell near the cone cylinder is fixedly connected with a spiral plate, and there is a gap between the spiral plate and an outer wall of the cone cylinder; the bottom of the shell is provided with a slope, and a lowest position of the slope is directly opposite to an outlet on the bottom of the shell; a top of the shell is provided with an inlet, and a side of the top of the shell where the inlet is located is provided with a light active component inlet.

In an embodiment, a cylindrical cavity is provided inside the separating cylinder; an end of the separating cylinder is provided with a second motor, and the second motor is fixedly connected with a rotary shaft; the rotary shaft is located in the cylindrical cavity, and is circumferentially provided with a spiral blade; an end of the cylindrical away from the second motor is fixedly provided with a compression spring, and a front end of the compression spring is fixedly connected with a pressing block; the pressing block is in sliding connection with an inner wall of the cylindrical cavity, and is in sliding connection with the rotary shaft; the second discharge port is arranged on a top of a side of the separating cylinder near the pressing block; and the liquid collecting tank and the separating cylinder are communicated through a fluid outlet.

In an embodiment, a first pipe is connected between the first discharge port and the return pipe.

In an embodiment, a second pipe is connected between the light active component inlet and the return pipe.

In an embodiment, a third pipe is connected between the sludge discharge pipe and the shell, and the third pipe is fixedly provided with a second valve.

In an embodiment, the return pipe is connected with a return pump.

The present disclosure has following beneficial effects.

Through the first separating mechanism and the second separating mechanism, the heavy inert materials at the bottom of the self-sustaining air flotation screening tank can be subjected to swirl separation, so that the liquid part, the solid part and the gas part can be completely separated, and then the useful active materials are conveyed to the reaction device; the device can separate the heavy inert materials twice, and the light active materials contained in the heavy inert materials can be completely separated, so that the practicability of the device is improved.

BRIEF DESCRIPTION OF THE DRAWINGS

To illustrate technical solutions in the embodiments of present disclosure or the technical solutions in the prior art more clearly, the accompanying drawings needed in the description of the embodiments will be briefly introduced below. Obviously, presented in the accompanying drawings described below are only some embodiments of the disclosure. For those of ordinary skill in the art, other drawings can be obtained according to these figures without paying creative effort.

Figure 1:
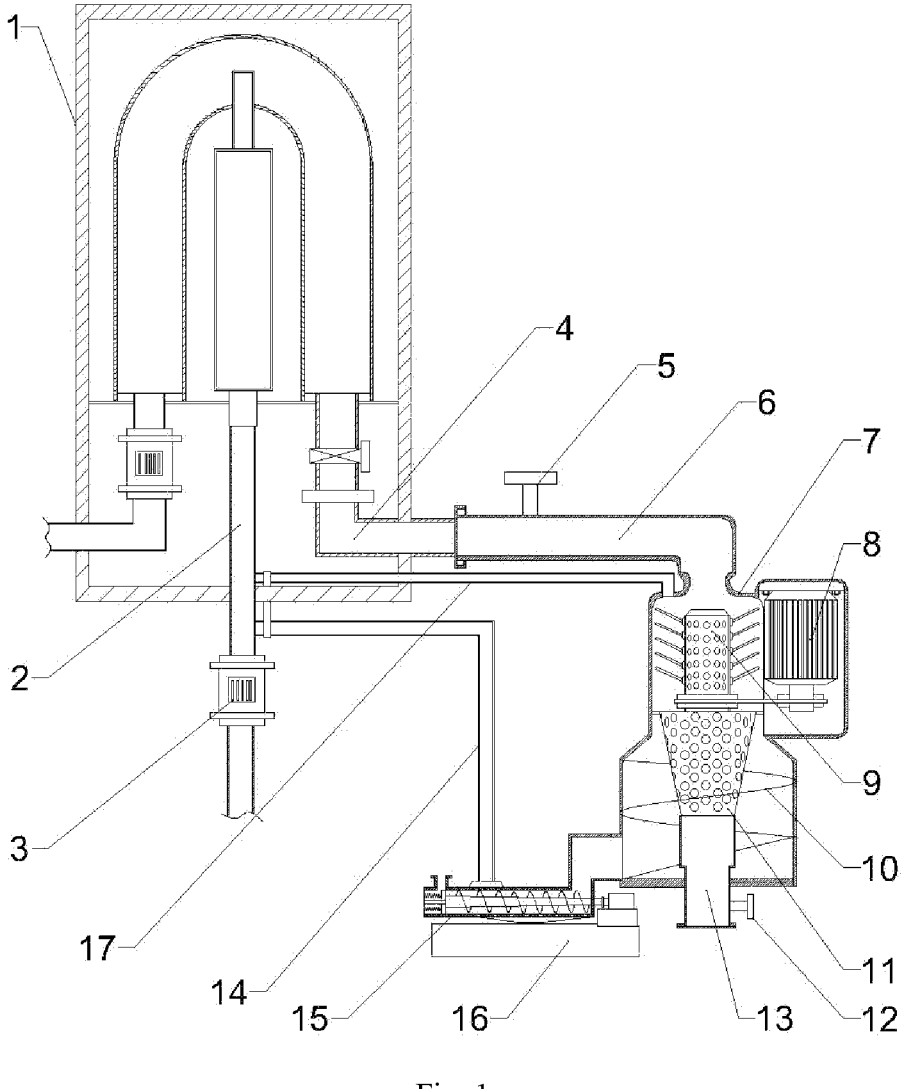
FIG. 1 schematically shows an inner structure of a device according to an embodiment of the present disclosure.

In the drawings: 1, Self-sustaining air flotation screening tank; 2, Return pipe; 3, Return pump; 4, Sludge discharge pipe; 5, Second valve; 6, Third pipe; 7, Shell; 8, First motor; 9, Rotating cylinder; 10, Spiral plate; 11, Cone cylinder; 12, First valve; 13, Cleaning pipe; 14, First pipe; 15, Separating cylinder; 16, Liquid collecting tank; 17, Second pipe; 18, Inlet; 19, Light active component inlet; 20, Stirring rod; 21, Through holes; 22, Outlet; 23, Slope; 24, Round hole; 25, Sprocket; 26, Chain; 27, Second motor; 28, Rotary shaft; 29, Spiral blade; 30, Fluid outlet; 31, First discharge port; 32, Second discharge port; 33, Spring; 34, Pressing block; and 35, Cross-bar.

DETAILED DESCRIPTION OF EMBODIMENTS

The present disclosure will be clearly and completely described below with reference to the embodiments and accompanying drawings. It's obvious that the embodiments described herein are only some embodiments rather than all embodiments of the disclosure. Based on the embodiments provided herein, all other embodiments obtained by one of ordinary skill in the art without making creative effort shall fall within the scope of the disclosure.

To make the above purposes, features and advantages of the disclosure more obvious and understandable, the disclosure will be further described in detail with reference to accompanying drawings and specific embodiments.

Figure 2:
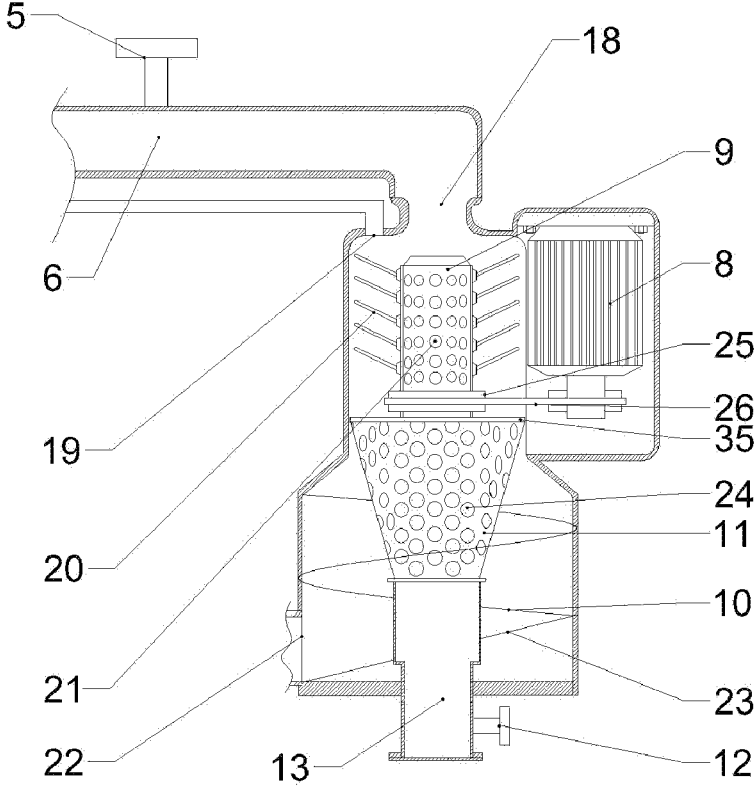
FIG. 2 schematically shows an inner structure of a first separating mechanism according to an embodiment of the present disclosure.
Figure 3:
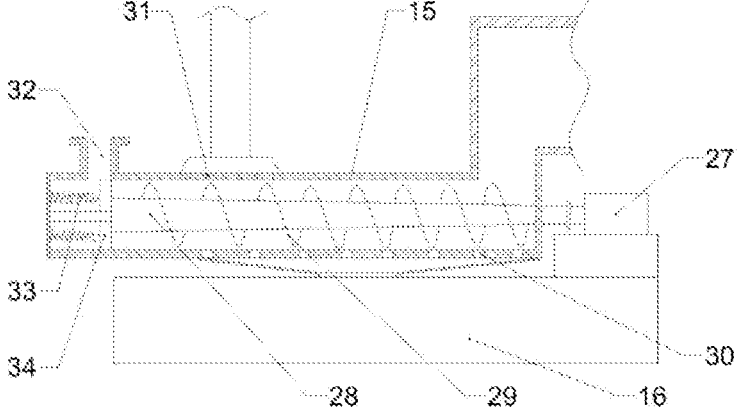
FIG. 3 schematically shows an inner structure of a second separating mechanism according to an embodiment of the present disclosure.
Figure 4:
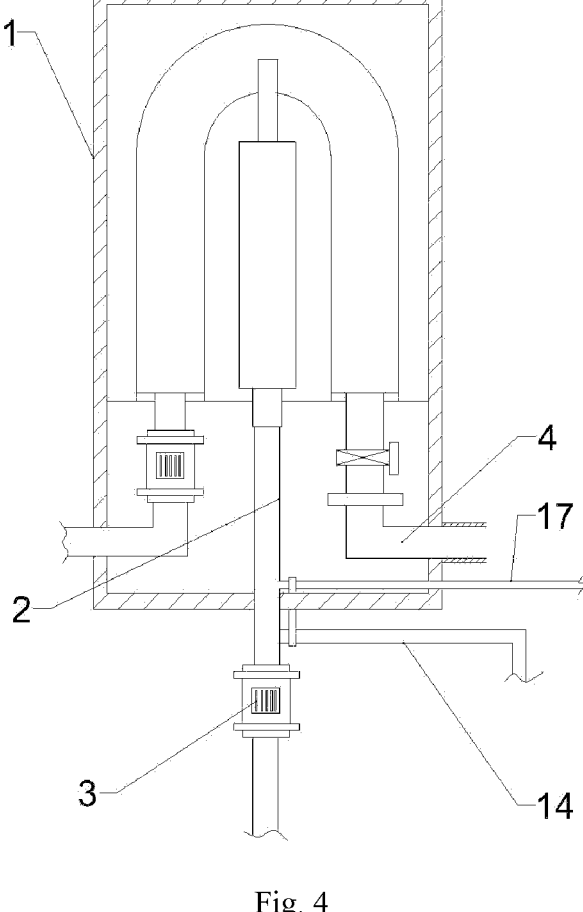
FIG. 4 schematically shows a self-sustaining air flotation screening tank according to an embodiment of the present disclosure.

According to FIGS. 1-4, this application provides an organic solid waste anaerobic digestion device with HRT uncoupled from SRT, which includes a self-sustaining air flotation screening tank equipped with a sludge discharge pipe 4 and a return pipe 2. The sludge discharge pipe 4 is connected with a first separating mechanism. A bottom of the first separating mechanism is connected with a second separating mechanism, and both two separating mechanisms are connected with the return pipe 2. By providing the first separating mechanism and the second separating mechanism, heavy inert materials on a bottom of a self-sustaining air flotation screening tank can be subjected to swirl separation, so that the liquid part, the solid part and the gas part can be completely separated, and then useful active materials are conveyed to the reaction device. The device can separate the heavy inert materials twice, and light active materials contained in the heavy inert materials can be completely separated, so that the practicability of the device is improved.

The first separating mechanism includes a shell 7, a first separating part and a second separating part. The first separating part and the second separating part are located in the shell 7 and are rotationally connected with the shell 7. The first separating part is located above the second separating part. The first separating part is communicated with the second separating part. The first separating mechanism includes a rotating cylinder 9. An outer wall of the rotating cylinder 9 is circumferentially fixedly connected with a plurality of stirring rods 20. A body of the rotating cylinder 9 is provided with a plurality of through holes 21. The plurality of through holes 21 and the plurality of stirring rods 20 are in staggered arrangement. Atop of the rotating cylinder 9 is closed, and a wall at a bottom of the rotating cylinder 9 is fixedly connected a sprocket 25. The sprocket 25 is in transmission connection with a first motor 8 through a chain 26, and the first motor 8 is fixedly connected with an outer side of the shell 7. The second separating mechanism includes a cone cylinder 11 and a top of the cone cylinder 11 is open. A wall of the cone cylinder 11 is provided with a plurality of round holes 24. The top of the cone cylinder 11 is fixedly connected with a cross-bar 35, and the cross-bar 35 is fixedly connected with the bottom of the rotating cylinder 9. A bottom of the cone cylinder 11 is rotatably connected with a cleaning pipe 13. An end the cone cylinder 11 away from the cone cylinder 11 penetrates a bottom of the shell 7 and is communicated with outside. The cleaning pipe 13 is provided with a first valve 12. The plurality of stirring rods 20 of the first separating part can break up and stir the heavy inert materials so that the light active material thereof can be further separated, and the liquid part inside can also be initially separated from the solid part. The second separating part and the first separating part is in synchronous rotation, and both two separating parts are in transmission connection with the first motor 8 through the chain 26. The rotating cylinder 9 is connected with the cone cylinder 11 through the cross-bar 35, and the cross-bar 35 can be cruciform. An inner of the shell near the cone cylinder 11 is fixedly connected with a spiral plate to improve an effect of separation.

The second separating mechanism includes a separating cylinder 15. In an embodiment, the separating cylinder 15 is a cyclone separator. A bottom of the separating cylinder 15 is connected with a liquid collecting tank 16 and a side of a top of the separating cylinder 15 is provided with a first discharge port 31 and a second discharge port 32. A cylindrical cavity is provided inside the separating cylinder 15. An end of the separating cylinder 15 is provided with a second motor 27, and the second motor 27 is fixedly connected with a rotary shaft 28. The rotary shaft 28 is located in the cylindrical cavity, and is circumferentially provided with a spiral blade 29 upwards. An end of the cylindrical cavity away from the second motor 27 is fixedly provided with a compression spring 33, and a front end of the compression spring 33 is fixedly connected with a pressing block 34. The pressing block 34 is in sliding connection with an inner wall of the cylindrical cavity, and is in sliding connection with the rotary shaft 28. The second discharge port 32 is arranged on a top of a side of the separating cylinder 15 near the pressing block 34. The liquid collecting tank 16 and the separating cylinder 15 are communicated through a fluid outlet 30. The shaft diameter of the rotary shaft 28 gradually increases from a side of the rotary shaft 28 near the second motor to its left, i.e., a cone shape. The heavy inert materials can be driven to achieve solid-liquid separation, and the light active components are further discharged.

An inner wall of the shell 7 near the cone cylinder 11 is fixedly connected with a spiral plate 10, and there is a gap between the spiral plate 10 and an outer wall of the cone cylinder 11. The bottom of the shell 7 is provided with a slope 23, and the lowest position of the slope 23 is directly opposite to an outlet 22 on the bottom of the shell 7. A top of the shell 7 is provided with an inlet 18, and a side of the top of the shell 7 where the inlet 18 is located is provided with a light active component inlet 19. The spiral plate 10 can drive the heavy inert materials slowly down to prevent materials from causing blocking at the bottom of the shell 7.

The cylindrical cavity is provided inside the separating cylinder 15. The end of the separating cylinder 15 is provided with the second motor 27, and the second motor 27 is fixedly connected with the rotary shaft 28. The rotary shaft 28 is located in the cylindrical cavity, and is circumferentially provided with a spiral blade 29 upwards. An end of the cylindrical cavity away from the second motor 27 is fixedly provided with a compression spring 33, and the front end of the compression spring 33 is fixedly connected with the pressing block 34. The pressing block 34 is in sliding connection with the inner wall of the cylindrical cavity, and is in sliding connection with the rotary shaft 28; the second discharge port 32 is arranged on the top of the cylinder 15 near the pressing block 34. The liquid collecting tank 16 and the separating cylinder 15 are communicated through the fluid outlet 30. When the heavy inert materials press the pressing block 34, the pressing block 34 will move backwards so that the heavy inert materials discharge from the second discharge port 32.

A first pipe 14 is connected between the first discharge port 31 and the return pipe 2. A second pipe 17 is connected between the light active component inlet 19 and the return pipe 2. A third pipe 6 is connected between the sludge discharge pipe 4 and the shell 7, and the third pipe is provided with a second valve 5. And the return pipe 2 is connected with a return pump 3.

Working process is as follows: in practical use, materials of the self-sustaining air flotation screening tank 1 are discharged from the sludge discharge pipe 4 and then enter the shell 7 through the third pipe 6. Firstly, the materials go through the first separating part which can break up the heavy inert materials, and the light active component can enter the return pipe 2 through the light active component inlet 19. Secondly, the heavy inert materials enter the second separating part and then can be subjected to swirl separation. Thirdly, the materials from last step enter the separating cylinder 15 through the outlet 22 to achieve solid-liquid separation, and the light active materials can flow back to the return pipe 2 through the first discharge port 31 again at the same time. Finally, the light active materials are transported back to the reaction device or the main tank through the return pipe 2.

In the description of the invention, it should be understood that, the orientation or position relationship indicated by the terms "lengthwise", "crosswise", "up", "down", "front", "back", "left", "right", "vertical", "horizontal", "top", "bottom", "inside", "outside" and so on are based on the orientation or position relationships shown in the accompanying drawings. It is only for describing easily, rather than indicating or implying the devices or components must have a particular orientation or be constructed and operated in particular orientation, therefore, it can not be understood as a limitation of the invention.

Described above are only preferred embodiments of the disclosure, which are not intended to limit the scope of the disclosure. It should be noted that various variations and modifications made by those skilled in the art without departing from the spirit of the disclosure shall fall within the scope of the disclosure defined by the appended claims.

What is claimed is:

1. An anaerobic digestion device for organic solid waste based on uncoupling of hydraulic retention time (HRT) from sludge retention time (SRT), comprising:

a self-sustaining air flotation screening tank;

wherein the self-sustaining air flotation screening tank is provided with a sludge discharge pipe and a return pipe; the sludge discharge pipe is connected with a first separating mechanism; a bottom of the first separating mechanism is connected with a second separating mechanism; the first separating mechanism and the second separating mechanism are both connected with the return pipe;

the first separating mechanism comprises a shell, a first separating part and a second separating part; the first separating part and the second separating part are located in the shell, and are rotationally connected with the shell; the first separating part is located above the second separating part; and the first separating part is communicated with the second separating part;

the second separating mechanism comprises a separating cylinder; a bottom of the separating cylinder is connected with a liquid collecting tank; a side of a top of the separating cylinder is provided with a first discharge port and a second discharge port; and the first separating part comprises a rotating cylinder; an outer wall of the rotating cylinder is circumferentially fixedly connected with a plurality of stirring rods; a body of the rotating cylinder is provided with a plurality of through holes; the plurality of through holes and the plurality of stirring rods are in staggered arrangement; a top of the rotating cylinder is closed, and a wall at a bottom of the rotating cylinder is fixedly connected with a sprocket; the sprocket is in transmission connection with a first motor through a chain; and the first motor is fixedly connected with an outer side of the shell.

2. The anaerobic digestion device of claim 1, wherein the second separating part comprises a cone cylinder; a top of the cone cylinder is open, and a wall of the cone cylinder is provided with a plurality of round holes; the top of the cone cylinder is fixedly connected with a cross-bar, and the cross-bar is fixedly connected with the bottom of the rotating cylinder; a bottom of the cone cylinder is rotatably connected with a cleaning pipe; an end of the cleaning pipe away from the cone cylinder penetrates a bottom of the shell and is communicated with outside; and the cleaning pipe is provided with a valve.

3. The anaerobic digestion device of claim 2, wherein a part of an inner wall of the shell near the cone cylinder is fixedly connected with a spiral plate, and there is a gap between the spiral plate and an outer wall of the cone; the bottom of the shell is provided with a slope, and a lowest position of the slope is directly opposite to an outlet on the bottom of the shell; a top of the shell is provided with an inlet, and a side of the top of the shell where the inlet is located is provided with a light active component inlet.

4. The anaerobic digestion device of claim 3, wherein a cylindrical cavity is provided inside the separating cylinder; an end of the separating cylinder is provided a second motor, and the second motor is fixedly connected with a rotary shaft; the rotary shaft is located in the cylindrical cavity, and is circumferentially provided with a spiral blade; an end of the cylindrical cavity away from the second motor is fixedly provided with a compression spring, and a front end of the compression spring is fixedly connected with a pressing block; the pressing block is in sliding connection with an inner wall of the cylindrical cavity, and is in sliding connection with the rotary shaft; the second discharge port is arranged on a top of a side of the separating cylinder near the pressing block; and the liquid collecting tank and the separating cylinder are communicated through a fluid outlet.

5. The anaerobic digestion device of claim 4, wherein a pipe is connected between the first discharge port and the return pipe.

6. The anaerobic digestion device of claim 3, wherein a pipe is connected between the light active component inlet and the return pipe.

7. The anaerobic digestion device of claim 1, wherein a pipe is connected between the sludge discharge pipe and the shell, and the pipe is fixedly provided with a valve.

8. The anaerobic digestion device of claim 1, wherein the return pipe is connected with a return pump.

* * * * *